United States Patent
Fukuta et al.

(10) Patent No.: US 10,473,597 B2
(45) Date of Patent: Nov. 12, 2019

(54) NEUTRON GRID, NEUTRON GRID STACK, NEUTRON GRID DEVICE, AND METHOD OF MANUFACTURING NEUTRON GRID

(71) Applicants: KABUSHIKI KAISHA TOSHIBA, Tokyo (JP); TOSHIBA MATERIALS CO., LTD., Yokohama-Shi (JP)

(72) Inventors: Yukihiro Fukuta, Yokohama (JP); Yoshitaka Adachi, Yokohama (JP); Nobuaki Nakashima, Yokohama (JP); Koichi Nittoh, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 16/139,281

(22) Filed: Sep. 24, 2018

(65) Prior Publication Data
US 2019/0025230 A1 Jan. 24, 2019

Related U.S. Application Data

(63) Continuation of application No. PCT/JP2017/012604, filed on Mar. 28, 2017.

(30) Foreign Application Priority Data

Mar. 29, 2016 (JP) .................................. 2016-065758

(51) Int. Cl.
*G01N 23/06* (2018.01)
*G01T 3/00* (2006.01)
(Continued)

(52) U.S. Cl.
CPC ............. *G01N 23/05* (2013.01); *G01N 23/09* (2013.01); *G01T 1/29* (2013.01); *G01T 3/00* (2013.01);
(Continued)

(58) Field of Classification Search
CPC .. G01N 23/05; G01N 23/09; G01N 2223/106; G01T 1/29; G01T 3/00; G01T 7/00
See application file for complete search history.

(56) References Cited

U.S. PATENT DOCUMENTS

2007/0104321 A1   5/2007   Spahn

FOREIGN PATENT DOCUMENTS

| CH | 201 101 A | 11/1938 |
|---|---|---|
| JP | 2007-130460 A1 | 5/2007 |

(Continued)

OTHER PUBLICATIONS

Engineering Tool Box, (2003). Young's Modulus—Tensile and Yield Strength for common Materials. [online] Available at: https://www.engineeringtoolbox.com/young-modulus-d_417.html [Accessed Dec. 20, 2018]. (Year: 2003).*

(Continued)

*Primary Examiner* — Mark R Gaworecki
(74) *Attorney, Agent, or Firm* — Burr & Brown, PLLC

(57) ABSTRACT

A neutron grid, comprises: a grid including: a plurality of spacers through which at least a part of first neutrons from a target passes; and a plurality of absorbers to absorb at least a part of second neutrons scattered thorough the target, the spacers and the absorbers being alternately arranged along a first direction and extending along a second direction intersecting with the first direction; and a pair of covers through which at least a part of the first neutrons and at least a part of the second neutrons pass, sandwiching the grid along a third direction intersecting with the first and second directions. A thermal expansion coefficient difference between one of the spacers and one of the absorbers is $\pm 9 \times 10^{-6}/°$ C. or less, or Young's modulus of the spacer is 100 GPa or more.

12 Claims, 5 Drawing Sheets

(51) Int. Cl.
  *G01T 1/29* (2006.01)
  *G01T 7/00* (2006.01)
  *G01N 23/09* (2018.01)
  *G01N 23/05* (2006.01)
(52) U.S. Cl.
  CPC .......... *G01T 7/00* (2013.01); *G01N 2223/106* (2013.01)

(56) References Cited

FOREIGN PATENT DOCUMENTS

| JP | 2008-232731 A1 | 10/2008 |
| JP | 2010-230328 A1 | 10/2010 |
| JP | 2013-181916 A1 | 9/2013 |

OTHER PUBLICATIONS

Engineering Tool Box, (2003). Coefficients of Linear Thermal Expansion. [online] Available at: https://www.engineeringtoolbox.com/linear-expansion-coefficients-d_95.html [Accessed Dec. 20, 2018]. (Year: 2003).*
International Search Report and Written Opinion (Application No. PCT/JP2017/012604) dated Jun. 20, 2017.
Partial Supplementary European Search Report (Application No. 17775067.6) dated Sep. 13, 2019.

\* cited by examiner

US 10,473,597 B2
NEUTRON GRID, NEUTRON GRID STACK, NEUTRON GRID DEVICE, AND METHOD OF MANUFACTURING NEUTRON GRID

CROSS-REFERENCE TO RELATED APPLICATIONS

This application is a continuation of prior International Application No. PCT/JP2017/012604, filed on Mar. 28, 2017 which is based upon and claims the benefit of priority from Japanese Patent Application No. 2016-065758, filed on Mar. 29, 2016; the entire contents of all of which are incorporated herein by reference.

FIELD OF THE INVENTION

Embodiments described herein generally relate to a neutron grid, a neutron grid stack, a neutron grid device, and a manufacturing method of the neutron grid.

BACKGROUND OF THE INVENTION

When radiation rays such as X-rays and gamma rays pass through a substance, absorption and scattering differ depending on a kind and a shape of the substance. It is possible to grasp a damaged state, a change, a filling state, and so on of the substance by recording the difference in the absorption and the scattering as, for example, photographs, video, digital files, and the like. Measurement of the absorption and scattering of X-rays is generally used as a method examining a state of an inside of a human body such as an X-ray photograph in a case of X-rays. This method of measuring a state of an inside without destroying a substance or a sample to be measured is called radiography or a nondestructive radiation photographing method.

In medical photographing using X-rays, primary X-rays are radially emitted from a focal point of an X-ray source, to be irradiated on a specimen. A part of the primary X-rays is absorbed by the specimen, and the remainder is attenuated as it is without changing an angle to pass through the specimen, and recorded by an image-receiving body. Meanwhile, when the primary X-rays are irradiated on the specimen, X-rays scatter in addition to being absorbed depending on the substance, and secondary X-rays, tertiary X-rays, and so on being scattered rays head for the image-receiving body while changing an angle from the primary X-rays.

When a transmission image of the specimen is to be obtained under this state, the secondary X-rays, the tertiary X-rays, and so on in addition to the primary X-rays are recorded on the image-receiving body. Accordingly, a clear transmission image cannot be obtained because a transmission image obtained by the scattered X-rays such as the secondary X-rays and the tertiary X-rays is overlapped with a transmission image obtained by the primary X-rays.

In this context, a grid is normally disposed between the specimen and the image-receiving body to obtain a clear transmission image by removing the scattered X-rays such as the secondary X-rays and the tertiary X-rays.

In a grid, a spacer part whose X-ray absorptance is low and absorption foil whose X-ray absorptance is high are arranged in a direction approximately in parallel to an irradiation direction of the primary X-rays, and they are layered in an approximately perpendicular direction to the irradiation direction. For example, fiber, resin, chip, or aluminum (Al) are used as the spacer, and foil containing a heavy element such as lead foil is used as the foil. As a result, the scattered X-rays such as the secondary X-rays and the tertiary X-rays having different angles from the primary X-rays are absorbed by the lead foil of the grid to be removed.

There are grids such as a focused grid where an angle of the grid is aligned with an angle of the primary X-rays in accordance with a distance from the focal point of the X-ray source to the image-receiving body, a parallel grid assuming that the primary X-rays are irradiated in parallel, and a tapered grid where heights of the lead foil at a center and at an outer side are different. Standards of the grids are described in JIS Z 4910:2015 as a guide.

There is also known a method to obtain a transmission image of a specimen by using neutrons as same as X-rays. This method is called neutron radiography, neutron imaging, or the like, and has been vigorously used in fields of fuel cell and engine containing hydrogen and hydrogen atoms in metal where water, resin, oil, alcohol, and so on are contained, and hydrogen storage which are almost impossible to photograph by conventional X-ray or gamma-ray radiography. This is because a scattering reaction of neutrons with hydrogen or the like having approximately the same mass is remarkable, and neutron has high sensitivity with water, plastic, and so on each containing hydrogen. These methods are suitable for imaging of specific neutron absorption materials such as gadolinium (Gd), cadmium (Cd), or boron (B).

However, there is a problem also in the case when the transmission image of the specimen is obtained by using neutrons as stated above that a clear transmission image cannot be obtained because scattering of neutrons occurs as same as the case of X-rays, and an image formed by the scattered neutrons overlaps with the transmission image. In a case of neutrons, unlike X-rays, a reaction with a constituent element of the specimen differs depending on energy of neutrons, and secondarily generated neutrons (scattered neutrons) also differ.

In a neutron radiography using a nuclear reactor as a neutron source, main components of used neutrons are thermal neutrons, and a main component of energy distribution thereof is 0.025 eV or less. However, there is a case when a very small amount of components of epithermal neutrons (EN) and fast neutrons (FN) which have higher energy than the thermal neutrons (TN) is contained also in the case of the nuclear reactor. When an accelerator is used as the neutron source, neutrons are widely distributed up to higher energy.

The fast neutrons react with hydrogen to be converted into the thermal neutrons. Accordingly, when the transmission image of the specimen is obtained by using the neutrons, the thermal neutrons are newly generated from the specimen different from the case using X-rays, an image formed by the thermal neutrons overlaps with a transmission image to be obtained by original thermal neutrons, resulting in that a clear transmission image cannot be obtained.

DETAILED DESCRIPTION OF THE INVENTION

A neutron grid, comprises: a grid including: a plurality of spacers through which at least a part of first neutrons from a target passes; and a plurality of absorbers to absorb at least a part of second neutrons scattered thorough the target, the spacers and the absorbers being alternately arranged along a first direction and extending along a second direction intersecting with the first direction; and a pair of covers through which at least a part of the first neutrons and at least a part of the second neutrons pass, sandwiching the grid along a third direction intersecting with the first and second directions. A thermal expansion coefficient difference between one of the spacers and one of the absorbers is $\pm 9 \times 10^{-6}/°$ C. or less, or Young's modulus of the spacer is 100 GPa or more.

(Neutron Grid)
<Constitution of Neutron Grid>

Figure 1:
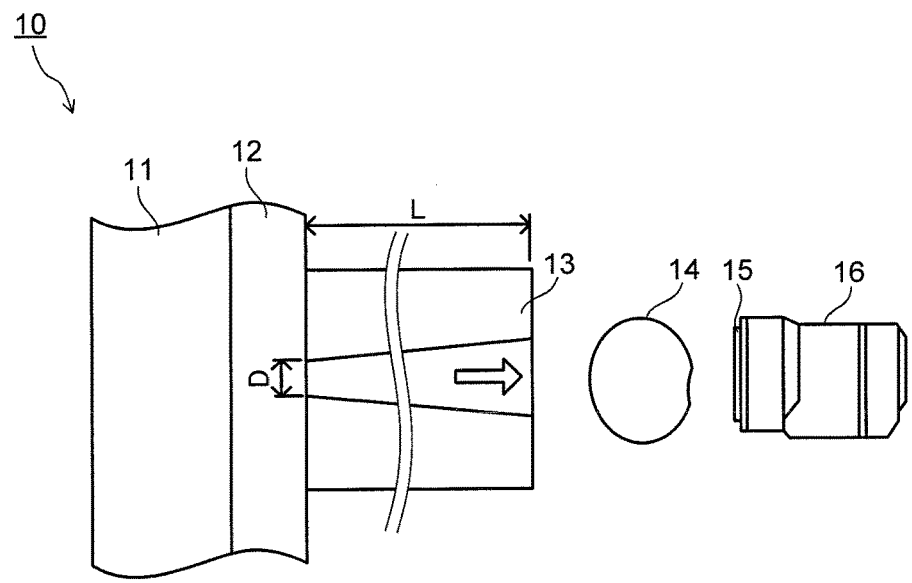
FIG. 1 is a constitutional diagram illustrating a structural example of a measurement system.
Figure 2:
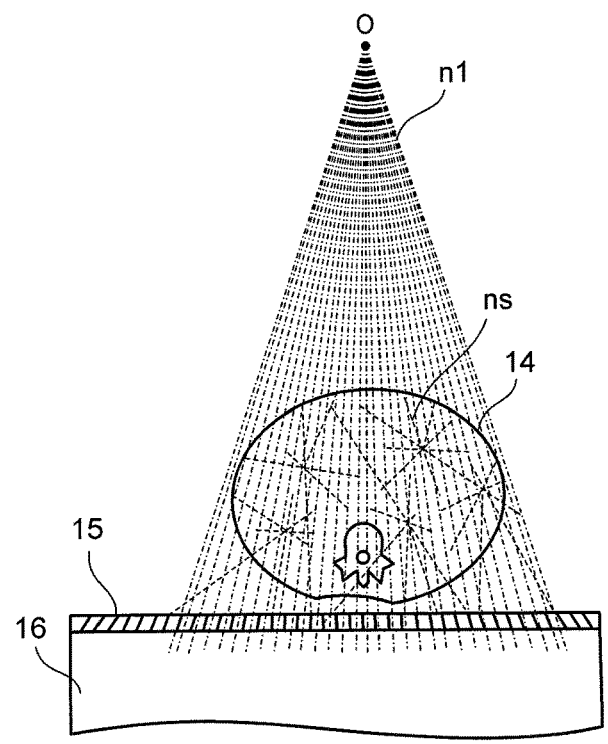
FIG. 2 is a schematic diagram to explain a method to obtain a transmission image of a specimen.
Figure 3:
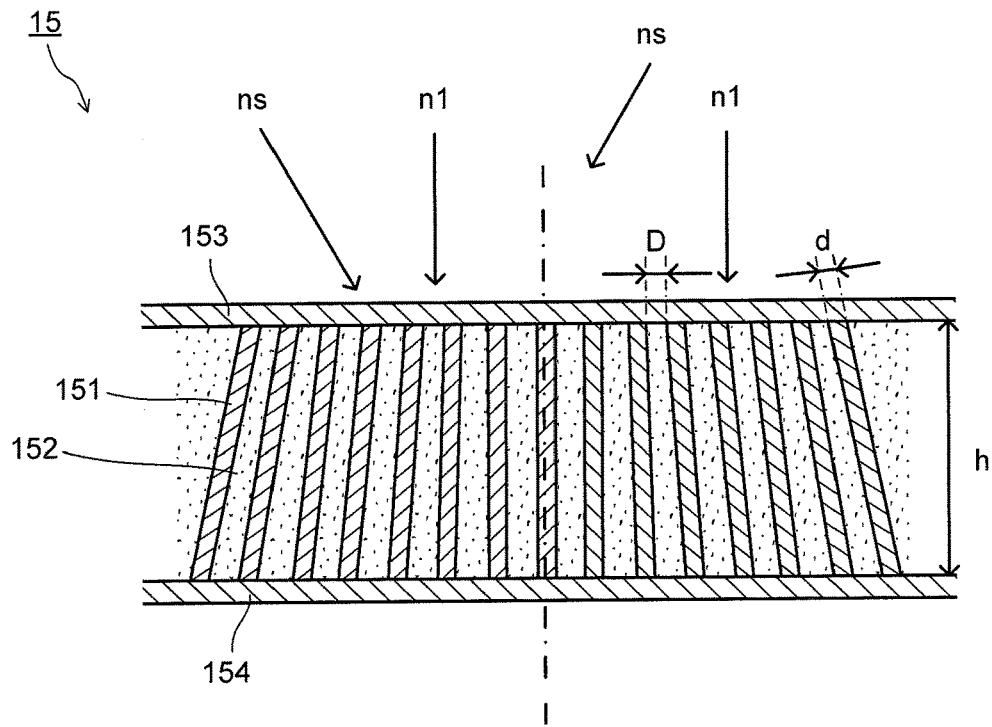
FIG. 3 is a cross-sectional schematic diagram illustrating a structural example of a neutron grid.
Figure 4:
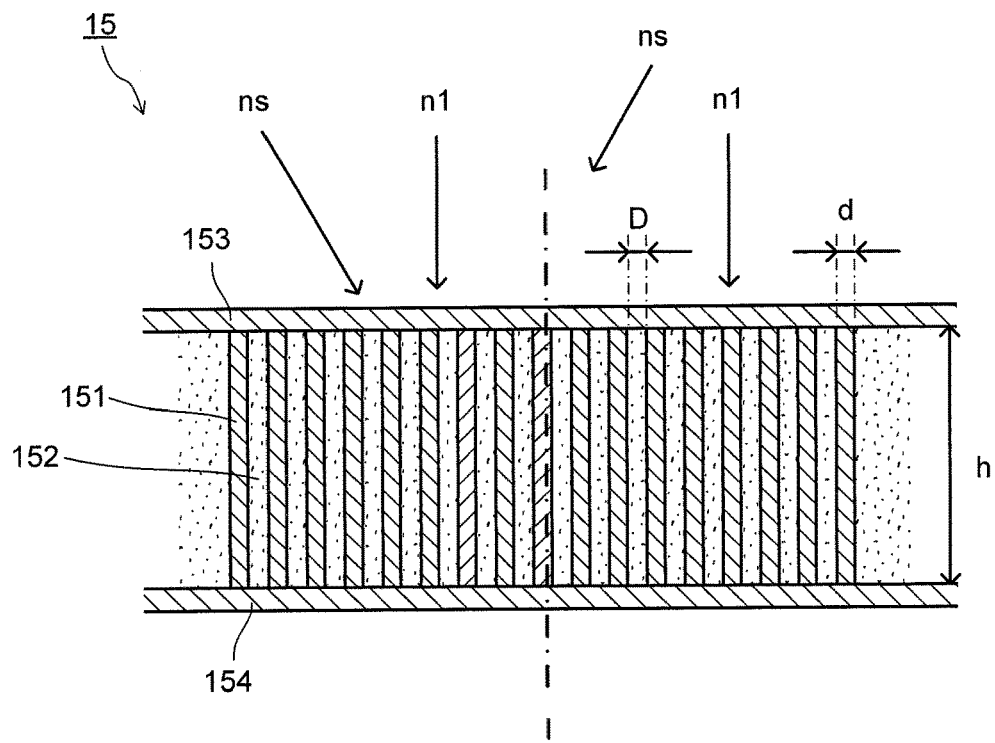
FIG. 4 is a cross-sectional schematic diagram illustrating another structural example of a neutron grid.

FIG. 1 is a schematic diagram illustrating a constitutional example of a neutron radiography measurement system. FIG. 1 illustrates an example where an image-receiving body using a neutron image intensifier (neutron I. I.) and a neutron source using a nuclear reactor are used. FIG. 2 is a schematic diagram to explain a method to obtain a transmission image of a target such as a specimen by using a measurement system. FIG. 3 and FIG. 4 are cross-sectional schematic diagrams each illustrating a structural example of a neutron grid used for the measurement system.

A measurement system 10 illustrated in FIG. 1 includes a neutron source 11 formed of a nuclear reactor, a moderator 12 disposed on a neutron emission side of the neutron source 11, and a collimator 13. FIG. 1 further illustrates a specimen 14 disposed on a neutron emission side of the collimator 13, a neutron grid 15 and an image-receiving body (neutron I. I.) 16 facing the collimator 13 and the like with the specimen 14 being interposed therebetween. In FIG. 1, a neutron emission width from the moderator 12 is defined as D, and a length of the collimator 13 is defined as L.

The neutron grid 15 includes a grid having a plurality of spacers 151 and a plurality of neutron absorbers 152, a cover 153, and a cover 154, as illustrated in FIG. 3.

The spacer 151 is able to transmit at least a part of first neutrons which pass through a target such as the specimen 14. The neutron absorber 152 is able to absorb at least a part of second neutrons which are scattered by the target.

The spacers 151 and the neutron absorbers 152 are alternately arranged along, for example, a first direction. As it can be seen from FIG. 1 and FIG. 2, an arrangement direction (first direction) of the plurality of spacers 151 and the plurality of neutron absorbers 152 is approximately perpendicular to an irradiation direction (incident direction) of at least a part of neutrons (first neutrons) from a radiation source such as the neutron source 11. The spacers 151 and the neutron absorbers 152 extend along, for example, a second direction which intersects with the first direction. The second direction may perpendicularly intersect with the first direction. Further, at least one of the spacers 151 and the neutron absorbers 152 extends from the cover 153 toward the cover 154 so as to widen an interval therebetween (a focusing type). At least one of the spacers 151 and the neutron absorbers 152 may extend from the cover 153 toward the cover 154 approximately in parallel to the irradiation direction (a parallel type) as illustrated in FIG. 4 without being limited to the focusing type. In FIG. 3, a width of the spacer 151 in the first direction is defined as d, a width of the neutron absorber 152 in the first direction is defined as D, an interval between the cover 153 and the cover 154 (a thickness of the grid) is defined as h, and a center axis of the neutron grid 15 is defined as I-I.

When a transmission image of a specimen is obtained by using neutrons, in particular, thermal neutrons, the neutron grid of the embodiment is disposed between the specimen and an image-receiving body such that the spacers and the neutron absorbers being components of the neutron grid extend approximately in parallel to the irradiation direction of the neutrons. In this case, the arrangement direction of the spacers and the neutron absorbers is approximately perpendicular to the irradiation direction of the neutrons.

Terms of "approximately parallel" and "approximately perpendicular" are defined in consideration of a case when neutrons are irradiated from a point radiation source O. That is, neutrons irradiated from the point radiation source O are radially irradiated on the specimen 14 to be radially incident on the neutron grid 15. In this case, neutrons passing through a center part of the specimen 14 are incident on the neutron grid 15 approximately perpendicular thereto, but neutrons passing through an end part of the specimen 14 are incident on the neutron grid 15 at a predetermined angle.

When neutrons which are incident at the predetermined angle with respect to the neutron grid 15 are taken into consideration, the arrangement direction of the plurality of spacers 151 and the plurality of neutron absorbers 152 is not necessarily perpendicular to the irradiation direction of the neutrons, and the spacers and the neutron absorbers are not necessarily extend in parallel to the irradiation direction of the neutrons, but such cases are also included in "approximately parallel" and "approximately perpendicular".

A thermal neutron mass attenuation coefficient of the neutron absorber 152 is 100 times or more as large as a thermal neutron mass attenuation coefficient of the spacer 151. Neutrons thereby pass through the spacers 151 but do not pass through the neutron absorbers 152 and are likely to be absorbed by the neutron absorbers 152.

The neutron grid 15 is able to exert a function as a grid to remove scattered neutrons (second neutrons) with respect to the neutrons by satisfying disposing conditions and physical conditions of the spacers 151 and the neutron absorbers 152.

The cover 153 and the cover 154, being a pair of covers, sandwich the plurality of spacers 151 and the plurality of neutron absorbers 152 along, for example, a third direction which perpendicularly intersects with the first direction and the second direction. The third direction may perpendicularly intersect with the first direction and the second direction. That is, the cover 153 and the cover 154 are overlapped in the irradiation direction of neutrons.

Fast neutrons generated at the neutron source (nuclear reactor) 11 are converted into thermal neutrons by the moderator 12, a part thereof is drawn by the collimator 13 to be irradiated on the specimen 14, and after passing through the specimen 14, recorded as an image by the image-receiving body (neutron image intensifier (I. I.)) 16 through the neutron grid 15. As a result, a transmission image of the specimen 14 can be obtained by the image-receiving body (neutron I. I.) 16.

When the neutron source 11 forms the point radiation source O due to the existence of the collimator 13 or the like, thermal neutrons n1 (first neutrons) irradiated from the point radiation source O radially spread to reach the specimen 14 as illustrated in FIG. 2. After that, a major part of the thermal neutrons n1 passes through the specimen 14 and reaches the image-receiving body 16 through the neutron grid 15. This is because the spacers 151 and the neutron absorbers 152 forming the neutron grid 15 extend approximately in parallel to the irradiation direction of the thermal neutrons n1, but the arrangement direction thereof is approximately perpendicular to the irradiation direction, and a part of the thermal neutrons n1 is absorbed by the neutron absorbers 152 but most of the remainder passes through the spacers 151.

A part of the thermal neutrons n1 scatters at a surface and an inside of the specimen 14 to be scattered thermal neutrons ns being the second neutrons. The scattered thermal neutrons ns randomly scatter in directions different from the irradiation direction of the original thermal neutrons n1 as it can be seen from FIG. 2. Accordingly, incident angles of the scattered thermal neutrons ns on the neutron grid 15 are not approximately parallel to the extending direction of the spacers 151 and the neutron absorbers 152 forming the neutron grid 15, and are not approximately perpendicular to the arrangement direction thereof. The scattered thermal neutrons ns, therefore, are obliquely incident on the neutron absorbers 152 to be absorbed without passing through the spacers 151. As a result, the image-receiving body 16 is able to obtain only the transmission image formed by the original thermal neutrons n1, and it is possible to prevent that an image formed by the scattered thermal neutrons ns overlaps with the transmission image. As a result, a clear transmission image of the specimen 14 can be obtained at the image-receiving body 16.

There is also a case when the scattered thermal neutrons ns are formed by scattering of the thermal neutrons n1 in a target such as the collimator 13 without being limited to the case when they are formed by the thermal neutrons n1 irradiated on the specimen 14. However, the scattered thermal neutrons ns formed as stated above are also absorbed to be removed by the neutron grid 15 based on the above-stated principle, and an image to be noise with respect to an objected transmission image is not formed.

Not all of the neutrons generated at the neutron source 11 are converted into thermal neutrons by the moderator 12, and they partly become epithermal neutrons and fast neutrons. However, such neutrons are also absorbed to be removed by the neutron grid 15 based on the above-stated principle, and an image to be noise with respect to an objected transmission image is not formed.

When components of epithermal neutrons and fast neutrons having higher energy than thermal neutrons generated from the neutron source react with hydrogen or the like to be converted into thermal neutrons, these subsidiary generated thermal neutrons randomly scatter in directions different from the irradiation direction of the neutrons, and are incident at a predetermined angle on the neutron absorbers of the neutron grid to be absorbed. Accordingly, an image formed by the subsidiary generated thermal neutrons does not overlap with the transmission image.

Since the spacers and the neutron absorbers of the neutron grid are disposed to extend in approximately parallel to the irradiation direction of the neutrons, the original neutrons irradiated from the neutron source as stated above, that is thermal neutrons, are partly absorbed by the neutron absorbers of the neutron grid, but not completely absorbed, and an objected transmission image of the specimen can be obtained.

<Composing Materials of Neutron Grid>

Figure 5:
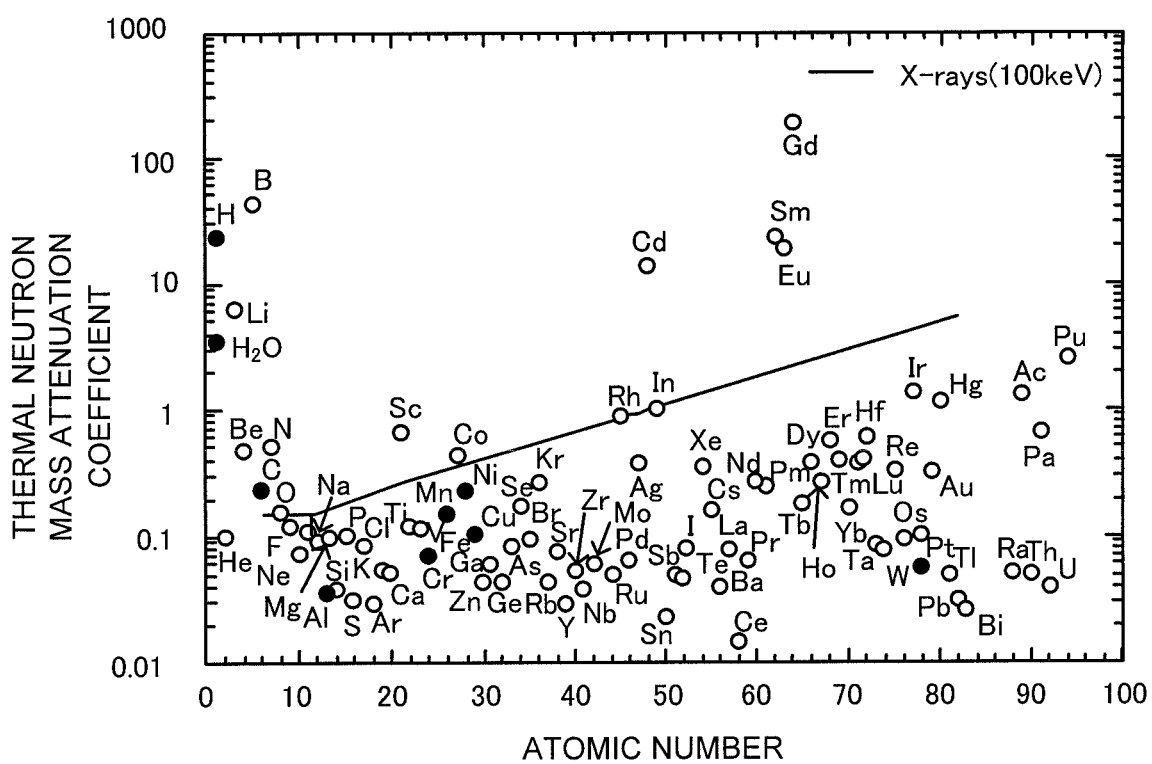
FIG. 5 is a graphic chart illustrating a relation between an element and a thermal neutron mass attenuation coefficient.

Next, composing materials of the neutron grid 15 are described. In FIG. 5, a horizontal axis shows an atomic number of an element, and a vertical axis shows a thermal neutron mass attenuation coefficient. An absorption coefficient at 100 kV X-ray is illustrated in the graph as a reference by a solid line.

It can be seen that high thermal neutron mass attenuation coefficients are shown in Li, B, Cd, In, Sm, and Gd with reference to FIG. 5. Meanwhile, low thermal neutron mass attenuation coefficients are shown in Al, Si, Sn, W, Au, Pb, and Bi.

Even in a case when there is the neutron absorber 152 having a second thermal neutron mass attenuation coefficient which is 100 times or more as large as a first thermal neutron mass attenuation coefficient of the spacer 151, a thickness of the spacer 151 per one piece is as thin as 1.0 mm or less, resulting in that warpage and deformation are likely to occur, variation in transmission directions of thermal neutrons occurs due to the warpage and deformation even when the spacers 151 are arranged in plural, constant transmission is difficult to obtain, and a clear transmission image is unlikely to be obtained. The spacers and the neutron absorbers being the components are therefore preferably unlikely to be warped and deformed in the neutron grid of the embodiment.

The composing materials of the neutron grid are preferably selected such that a difference between a thermal expansion coefficient of the spacer 151 and a thermal expansion coefficient of the neutron absorber 152 is $\pm 9 \times 10^{-6}/°$ C. or less, or Young's modulus of the spacer 151 is 100 GPa or more in addition to considering only the thermal neutron mass attenuation coefficients. The warpage and deformation of the spacer 151 and the neutron absorber 152 are thereby able to be suppressed. It is more preferable that the difference between the thermal expansion coefficient of the spacer 151 and the thermal expansion coefficient of the neutron absorber 152 is $\pm 9 \times 10^{-6}/°$ C. or less, and the Young's modulus of the spacer 151 is 100 GPa or more. When the difference in the thermal expansion coefficients between the spacer 151 and the neutron absorber 152 is larger than $\pm 9 \times 10^{-6}/°$ C., the warpage and deformation are likely to occur due to thermal effect, and when the Young's modulus of the spacer 151 is less than 100 GPa, the warpage and deformation are likely to occur due to the thermal effect and an external stress, resulting in that an image to be noise with respect to the transmission image of neutrons are likely to be formed in both cases.

Table 1 lists thermal expansion coefficients and Young's moduli of materials each having a high thermal neutron mass attenuation coefficient. Table 2 lists thermal expansion coefficients and Young's moduli of materials each having a low thermal neutron mass attenuation coefficient. From FIG. 5 and Tables 1, 2, the spacer 151 preferably contains at least one kind of materials or an element from among Si, W, and ceramics (at least one selected from the group consisting of $Al_2O_3$, AlN, SiC, and $Y_2O_3$), and the neutron absorber 152 preferably contains at least one kind of materials or an element from among B, Gd, Sm, Li, and Cd. Ta or a material containing Ta which is used as a fast neutron absorber can be used as the neutron absorber 152.

TABLE 1

| MATERIAL | THERMAL EXPANSION COEFFICIENT [$10^{-6}/°$ C.] (20-100° C.) | YOUNG'S MODULUS [GPa] |
|---|---|---|
| Li | 56.0 | 12 |
| B | 6.5 | 185 |
| Cd | 31.0 | 62 |
| In | 24.8 | 10 |
| Sm | 12.7 | 34 |
| Gd | 9.4 | 56 |

TABLE 2

| MATERIAL | THERMAL EXPANSION COEFFICIENT [$10^{-6}/°$ C.] (20-100° C.) | YOUNG'S MODULUS [GPa] |
|---|---|---|
| Al | 23.5 | 76 |
| Si | 9.6 | 185 |
| Sn | 23.5 | 61 |
| W | 4.5 | 403 |
| Au | 14.1 | 88 |
| Pb | 29.0 | 16 |
| Bi | 13.4 | 34 |
| Y | 10.6 | 63 |
| $Al_2O_3$ | 7.2 | 470 |
| SiC | 3.7 | 440 |
| AlN | 4.6 | 320 |
| $Y_2O_3$ | 7.2 | 160 |
| Ta | 6.5 | 181 |

The spacer 151 and the neutron absorber 152 may be formed of a simplex metallic element included in the above, or an alloy or other compounds as long as the above-stated elements are contained.

The neutron absorber 152 is preferably formed of a film body containing at least one of gadolinium oxide ($Gd_2O_3$), boron carbide ($^{10}B_4C$) containing enriched boron, B, and Gd in the context of chemical stability, easiness to obtain a raw material at a forming time, easiness to form, and the like.

Figure 6:
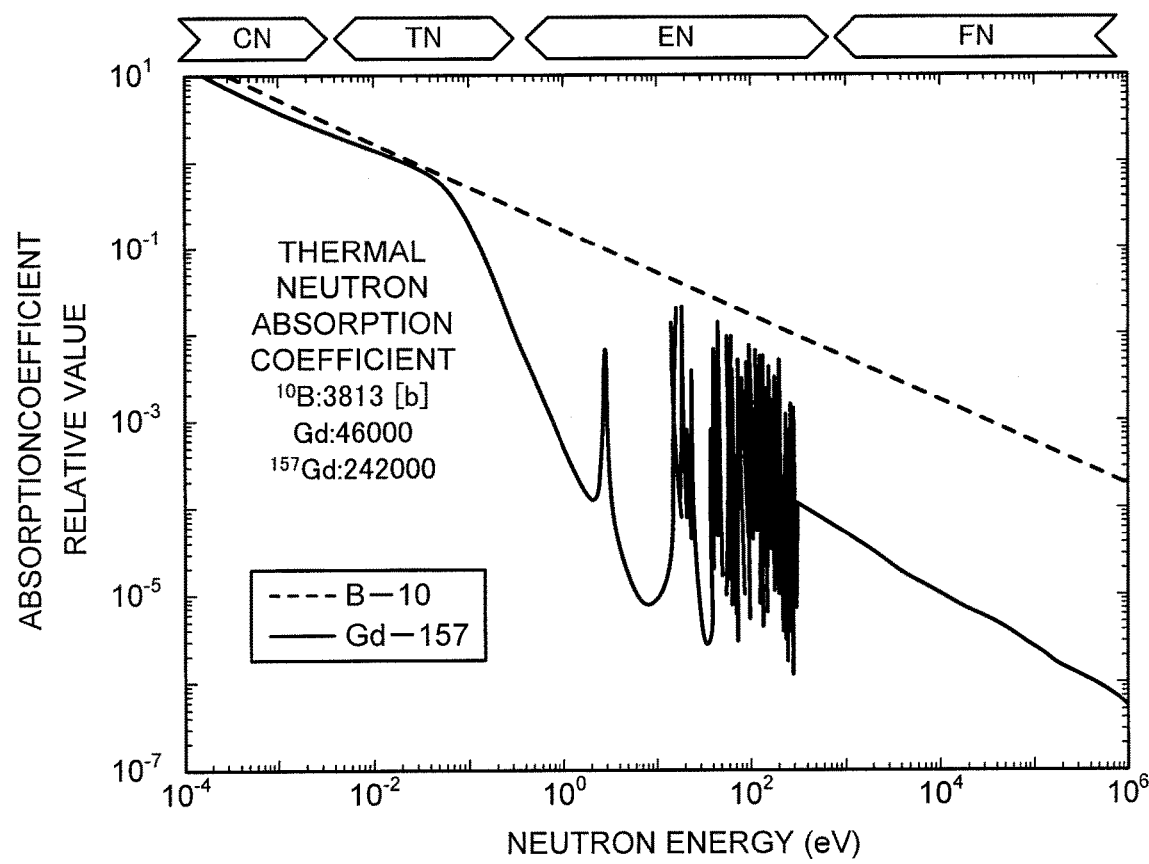
FIG. 6 is a view illustrating a relation between neutron energy and an absorption coefficient.

FIG. 6 is a view illustrating relative absorption characteristics with respect to neutron energy regarding boron (B) and gadolinium (Gd). FIG. 6 illustrates a relation between the neutron energy and a relative value of an absorption coefficient corresponding to each of cold neutrons (CN), thermal neutrons (TN), epithermal neutrons (EN), and fast neutrons (FN) when the thermal neutron energy of 0.025 eV is normalized to be 1. In a case of boron (B), B-10 being an isotope mainly absorbs neutrons, and B-11 seldom absorbs. Also in a case of gadolinium (Gd), Gd-157 being an isotope largely absorbs. The absorption coefficients of thermal neutrons illustrated in FIG. 6 are each represented by a unit of [b] (barn), and the larger this numeric value is, the more thermal neutrons are absorbed. Naturally existing gadolinium (Gd) has the absorption coefficient of about ten times or more as large as that of B-10.

At an energy region higher than a region of epithermal neutrons having higher energy than thermal neutrons, the absorption coefficient of gadolinium (Gd) becomes extremely smaller compared to boron (B). Accordingly, when the neutron grid 15 is used at higher neutron energy than thermal neutrons, the neutron absorber is preferably formed of a material containing B-10. Conversely, when the neutron grid 15 is used at lower neutron energy than thermal neutrons, gadolinium (Gd) having large absorption coefficient at such energy region is desirable.

The cover 153 and the cover 154 each preferably contain a material having a large atomic number which transmits neutrons but does not transmit X-rays and gamma rays. A space where neutrons are irradiated generally contains a lot of X-rays and gamma rays in addition to neutrons. Accordingly, the cover 153 and the cover 154 preferably remove noise due to X-rays and gamma rays. The cover 153 and the cover 154 are preferably formed of a material such as, for example, tungsten (W), lead (Pb), or bismuth (Bi), or an alloy having them as main components in the context of the above.

The cover 153 and the cover 154 can be formed by using aluminum (Al) as a support member, and forming the material such as tungsten (W), lead (Pb), or bismuth (Bi), or the alloy having them as the main components into a film state on the support member, or forming into a plate member to be adhered on the support member. The material may be only aluminum (Al) for a reduction in weight.

<Modification Example of Neutron Grid>

The neutron grid 15 can be used independently, but at least two or more of the neutron grids 15 are combined and layered such that the spacers 151 and the neutron absorbers 152 forming each neutron grid 15 intersect to form a grid stack. In this case, the absorption and removal of not only the scattered thermal neutrons ns in one direction but also the scattered thermal neutrons ns in the other directions can be performed. For example, when two neutron grids 15 are layered such that the spacers 151 and the neutron absorbers 152 forming each neutron grid 15 are orthogonal with each other, two-dimensional absorption and removal of the scattered thermal neutrons ns can be performed in two directions of an X direction and a Y direction.

(Manufacturing Method of Neutron Grid)

Next, a manufacturing method of the neutron grid 15 is described.

<First Manufacturing Method>

A first manufacturing method of the neutron grid 15 includes: a step of repeating a step of forming a film body of the neutron absorber 152 containing a material applicable to the neutron absorber 152 by using a vapor deposition method on a surface of the spacer 151, by each spacer 151; a step of forming a grid by arranging the spacers 151 and the neutron absorbers 152 along a first direction; and a step of sandwiching the grid by the cover 153 and the cover 154 along a third direction.

According to the first manufacturing method, the neutron absorber 152 is formed as the film body, and the film body becomes a state where constituent atoms are densely filled because the vapor deposition method is used. Accordingly, a number density of atoms contributing to the neutron absorption in the neutron absorber 152 becomes large, and scattered thermal neutrons or the like can be sufficiently absorbed even if a thickness of the film body is made small. Actually, the scattered thermal neutrons ns can be absorbed and removed in a range of at least about 30% to 80% by setting the thickness of the film body (a width of the film body in the first direction) in a range of 0.01 μm to 30 μm.

A ratio of the absorption and removal of the scattered thermal neutrons ns does not increase largely exceeding 80% even if the thickness of the film body exceeds 30 μm. Accordingly, an upper limit of the thickness of the neutron absorber 152 formed as the film body is preferably set to be approximately 30 μm in the context of use efficiency or the like of raw materials. On the other hand, when the thickness of the neutron absorber 152 as the film body is smaller than 0.01 μm, the ratio of the absorption and removal of the scattered thermal neutrons ns decreases, and there is a case when the neutron grid 15 in itself does not exert its original function.

Figure 7:
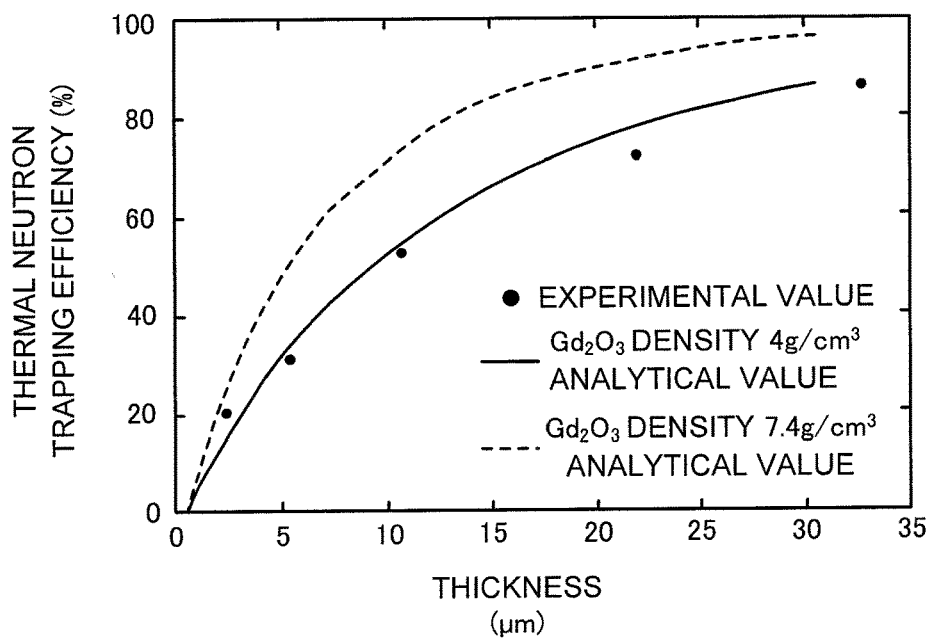
FIG. 7 is a view illustrating a relation between a film thickness and trapping efficiency of thermal neutrons in a stack.

FIG. 7 is a result where trapping efficiency of thermal neutrons in a stack obtained by vapor depositing gadolinium oxide ($Gd_2O_3$) on an aluminum substrate is measured with a He-3 neutron detector. Though a theoretical density of gadolinium oxide ($Gd_2O_3$) is 7.4 g/cm$^3$, an effective density coincides with 4 g/cm$^3$ from experimental results. When a thickness of gadolinium oxide ($Gd_2O_3$) is 5 µm, trapping (absorption) of about 30% is verified, and trapping (absorption) of about 80% is verified when the thickness is 30 µm as it can be seen from the results.

In FIG. 7, there is illustrated a case when thermal neutrons are perpendicularly incident on a film surface of the stack (in parallel to a thickness direction of the stack). However, the actual scattered thermal neutrons ns are obliquely incident on the neutron grid 15, that is, the neutron absorbers 152, resulting in that an effective thickness of each neutron absorber 152 with respect to the scattered thermal neutrons ns increases compared to the case of a perpendicular incident as illustrated in FIG. 7.

In FIG. 7, in case when the trapping (absorption) of about 30% is verified when the thickness of gadolinium oxide ($Gd_2O_3$) in the stack is 5 µm and the trapping (absorption) of 80% is verified when the thickness is 30 µm, the effective thickness with respect to the scattered thermal neutrons ns becomes 5 µm or more even when the thickness is 0.01 µm being a lower limit value in particular at the neutron absorber 152 in the actual neutron grid 15. The absorption and removal efficiency of the actual scattered thermal neutrons ns at the lower limit value of 0.01 µm, therefore, becomes 30% or more.

It is assumed that the scattered thermal neutrons ns can be absorbed and removed in a range of at least about 30% to 80% by setting the thickness of the film body of the neutron absorber 152 in a range of 0.01 µm to 30 µm, based on a study as stated above obtained from FIG. 7.

According to this method of forming the neutron absorber 152 as the film body through the vapor deposition method, the vapor deposition is performed for, for example, at least one of the above-stated materials or a raw material containing an element from among gadolinium oxide ($Gd_2O_3$), boron carbide ($^{10}B_4C$) containing enriched boron, B, and Gd. As the vapor deposition method, there can be used general methods such as a vacuum deposition method, a sputtering method, and a CVD method.

<Second Manufacturing Method>

A second manufacturing method of the neutron grid 15 includes: a step of repeating a step of mixing at least one kind of materials or powder containing an element from among gadolinium oxide ($Gd_2O_3$), gadolinium oxysulfide ($Gd_2O_2S$), and Gd each with a grain size of 10 µm or less, or at least one kind of materials or powder containing an element from among boron carbide ($^{10}B_4C$) and boron nitride ($^{10}BN$) containing enriched boron, and B each with a grain size of 10 µM or less and a binder, and forming a film body of the neutron absorber 152 on the spacer 151 through a precipitation method by using the mixture, by each spacer 151; a step of forming a grid by arranging the spacers 151 and the neutron absorbers 152 along a first direction; and a step of sandwiching the grid with the cover 153 and the cover 154 along a third direction. The film body of the neutron absorber 152 may be formed through the precipitation method by using other materials as long as the materials are applicable to the neutron absorber 152.

The precipitation method is a publicly-known film body forming method, and the spacer 151 is located at a bottom in a solution, powder of gadolinium oxide ($Gd_2O_3$) or the like is dispersed in the solution, the powder is precipitated after a while, a supernatant liquid is drained off to precipitate and adhere the powder on the spacer 151.

This method is effective when the spacer 151 is formed of a low-melting-point substance such as an alloy of tin or lead. When the vapor deposition method, particularly the vacuum deposition method is used, the spacer 151 being the substrate is necessary to be heated to high-temperature, but when the spacer 151 is formed of the low-melting-point substance as stated above, there is a possibility that an objected neutron grid 15 cannot be formed because the spacer 151 may be bent or partially melted due to the heating.

Meanwhile, since this method does not perform the heating operation for the spacer 151, the spacer 151 is not melted or the like when the neutron absorber 152 is formed even when the spacer 151 is formed of the low-melting-point substance. Accordingly, selectivity of materials usable for the spacer 151 increases.

However, in this method, the number density of the composing atoms of the neutron absorber 152 decreases compared to the first manufacturing method where the film body of the neutron absorber 152 is formed through the vapor deposition method. Accordingly, in this method, the thickness of the film body (a width of the film body in the first direction) is set to 100 µm to 500 µm so as to obtain the neutron absorption efficiency as same as the first manufacturing method.

<Third Manufacturing Method>

A third manufacturing method to manufacture the neutron grid 15 includes: a step of repeating a step of mixing at least one kind of materials or powder containing an element from among gadolinium oxide ($Gd_2O_3$), gadolinium oxysulfide ($Gd_2O_2S$), and Gd with a grain size of 10 µm or less, or at least one kind of materials or powder containing an element from among boron carbide ($^{10}B_4C$) and boron nitride ($^{10}BN$) containing enriched boron, and B with a grain size of 10 µm or less with a binder, and forming a film body of the neutron absorber 152 on the spacer 151 through a printing method by using the mixture, by each spacer 151; a step of forming a grid by arranging the spacers 151 and the neutron absorbers 152 along a first direction; and a step of sandwiching the grid with the cover 153 and the cover 154 along a third direction. The film body of the neutron absorber 152 may be formed through the printing method by using other materials as long as the materials are applicable to the neutron absorber 152.

Also in this method, since the heating operation is not performed for the spacer 151 as same as the second manufacturing method, the spacer 151 is not melted or the like when the neutron absorber 152 is formed even when the spacer 151 is formed of the low-melting-point substance. Accordingly, selectivity of materials usable for the spacer 151 increases.

However, also in this method, the number density of the composing atoms of the neutron absorber 152 decreases compared to the first manufacturing method where the film body of the neutron absorber 152 is formed through the vapor deposition method. Accordingly, in this method, the thickness of the film body (the width of the film body in the first direction) is set to 100 µm to 500 µm so as to obtain the neutron absorption efficiency as same as the first manufacturing method. Publicly-known methods such as a screen printing method can be used as the printing method.

(Neutron Grid Device)

Figure 8:
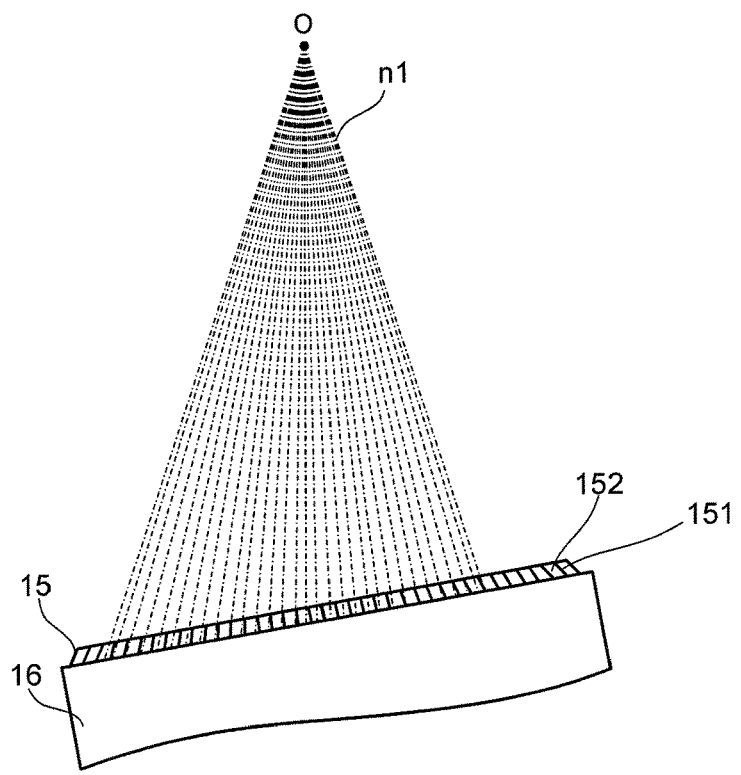
FIG. 8 is a schematic diagram to explain another method to obtain a transmission image of a specimen.

FIG. 8 is a schematic diagram to explain another method to obtain a transmission image of a target such as a specimen by using a measurement system. As illustrated in FIG. 8, when an irradiation direction of the thermal neutrons n1 irradiated from the neutron source 11 (the point radiation source O in this example) and a focusing direction of the neutron grid 15 deviate, the thermal neutrons n1 are not incident approximately in parallel to the extending direction of the spacers 151 and the neutron absorbers 152, and intersect with the extending direction at a predetermined angle to be incident. Under this state, the thermal neutrons n1 cannot pass through the neutron grid 15, and a transmission image of the specimen 14 (not illustrated in FIG. 8) cannot be obtained at the image-receiving body 16.

In such a case, the neutron grid 15 is used while being attached to a controller such as a rotation and linear driving device such that an angle and a front and rear distances of the neutron grid 15 can be remotely adjusted. A position of the neutron grid 15 is adjusted by the controller, resulting in that an axial direction of a center axis I-I of the neutron grid 15 is adjusted to have a positional relation coinciding with the incident direction of the thermal neutron n1, for example, as illustrated in FIG. 2 and the function of the neutron grid 15 is fully exhibited to obtain a clear transmission image of the specimen 14 on the image-receiving body 16 even when the irradiation direction of the thermal neutrons n1 and the focusing direction of the neutron grid 15 are in the relation as illustrated in FIG. 8 at the beginning.

As it has been described hereinabove, the neutron grid according to the embodiment of the present invention is used, and thereby, scattered radiation of neutrons causing noise of a transmission image can be removed without scattering due to warpage, deformation of components of the neutron grid when the transmission image of a specimen is obtained by using neutrons, particularly thermal neutrons.

While the present invention has been described in detail based on the concrete examples, the present invention is not limited to these concrete examples, and various modifications and changes may be made without departing from the spirit of the invention.

What is claimed is:

1. A neutron grid, comprising:
   a grid including: a plurality of spacers through which at least a part of first neutrons from a target passes; and a plurality of absorbers to absorb at least a part of second neutrons scattered thorough the target, the spacers and the absorbers being alternately arranged along a first direction and extending along a second direction intersecting with the first direction; and
   a pair of covers through which at least a part of the first neutrons and at least a part of the second neutrons pass, sandwiching the grid along a third direction intersecting with the first and second directions, wherein
   the spacers contain W and at least one selected from the group consisting of Si, $Al_2O_3$, AlN, SiC, and $Y_2O_3$,
   the absorbers contain Ta, or Ta and at least one selected from the group consisting of B, Gd, Sm, Li, Cd, $Gd_2O_3$, and $^{10}B_4C$,
   the covers contain Al, or Al and at least one selected from the group consisting of W, Pb and Bi, and
   a thermal expansion coefficient difference between one of the spacers and one of the absorbers is $\pm 9\times 10^{-6}/°$ C. or less, or Young's modulus of one of the spacers is 100 GPa or more.

2. The neutron grid according to claim 1, wherein the thermal expansion coefficient difference is $\pm 9\times 10^{-6}/°$ C. or less, and the Young's modulus of one of the spacers is 100 GPa or more.

3. The neutron grid according to claim 1, wherein the first neutrons and the second neutrons include thermal neutrons.

4. The neutron grid according to claim 3, wherein a thermal neutron mass attenuation coefficient of one of the absorbers is 100 times or more as large as a thermal neutron mass attenuation coefficient of one of the spacers.

5. The neutron grid according to claim 1, wherein a width of one of the absorbers in the first direction is 0.01 µm or more and 30 µm or less.

6. The neutron grid according to claim 1, wherein a width of one of the absorbers in the first direction is 100 µm or more and 500 µm or less.

7. The neutron grid according to claim 1, wherein at least one of the spacers and the absorbers extend along an incident direction of the first neutrons.

8. The neutron grid according to claim 1, wherein at least one of the spacers and the absorbers extend in parallel with each other from one of the covers to the other thereof.

9. The neutron grid according to claim 1, wherein at least one of the spacers and the absorbers extend to widen an interval therebetween from one of the covers to the other of the covers.

10. A neutron grid stack, comprising:
    a first neutron grid according to claim 1; and
    a second neutron grid according to claim 1, being stacked on the first neutron grid.

11. A neutron grid device, comprising:
    a neutron grid according to claim 1; and
    a controller to adjust a direction of a center axis of the neutron grid onto an incident direction of the first neutrons.

12. A method of manufacturing the neutron grid according to claim 1, comprising:
    forming the absorbers on the spacers using a vapor deposition method, a precipitation method, or a printing method;
    arranging the spacers and the absorbers along the first direction to form the grid; and
    sandwiching the grid with the covers along the third direction.

* * * * *